United States Patent [19]

Zörner

[11] 4,110,619
[45] Aug. 29, 1978

[54] METHOD OF COMPENSATING FOR CARRIER-GAS-COMPOSITION DEPENDENCE DUE TO THE COLLISION-BROADENING EFFECT IN NON-DISPERSIVE INFRARED PHOTOMETERS HAVING A DETECTOR COMPRISED OF TWO ABSORPTION CHAMBERS ARRANGED ONE BEHIND THE OTHER

[75] Inventor: Karl-Heinz Zörner, Norderstedt, Fed. Rep. of Germany

[73] Assignee: H. Maihak AG, Hamburg, Fed. Rep. of Germany

[21] Appl. No.: 763,585

[22] Filed: Jan. 28, 1977

Related U.S. Application Data

[63] Continuation-in-part of Ser. No. 744,175, Nov. 22, 1976, abandoned.

[30] Foreign Application Priority Data

Nov. 21, 1975 [DE] Fed. Rep. of Germany ....... 2552165

[51] Int. Cl.² ............................................. G01N 21/26
[52] U.S. Cl. .................................................. 250/344
[58] Field of Search ................ 250/344, 343, 345, 338

[56] References Cited

U.S. PATENT DOCUMENTS 3,898,462  8/1975  Ishida et al. ......................... 250/344
3,968,370  7/1976  Luft ..................................... 250/344

Primary Examiner—Davis L. Willis
Attorney, Agent, or Firm—Michael J. Striker

[57] ABSTRACT

The photometer comprises a light source, a reference cuvette containing a reference gas, a measurement cuvette containing a gas component whose concentration is to be measured accompanied by a carrier gas, a light modulator for effecting antiphase modulation of the infrared light passing through the two cuvettes, and a detector arrangement comprised of two gas-filled absorption chambers arranged one behind the other as well as a transducer for converting pressure changes induced in the absorption chambers into a measurement signal. The carrier gas consists of a plurality of component gases whose relative proportions fluctuate. The gas in the absorption chambers includes a gas component identical to the gas whose concentration is to be measured in the measurement cuvette, accompanied by an inert gas. The concentration of the infrared-active gas in the absorption chambers is repeatedly adjusted, until the measurement signal is made substantially independent of fluctuations in the relative proportions of the carrier-gas components.

10 Claims, 3 Drawing Figures

METHOD OF COMPENSATING FOR CARRIER-GAS-COMPOSITION DEPENDENCE DUE TO THE COLLISION-BROADENING EFFECT IN NON-DISPERSIVE INFRARED PHOTOMETERS HAVING A DETECTOR COMPRISED OF TWO ABSORPTION CHAMBERS ARRANGED ONE BEHIND THE OTHER

The application is a continuation-in-part of application Ser. No. 744,175 filed Nov. 22, 1976, now abandoned.

BACKGROUND OF THE INVENTION

The present invention relates to nondispersive infrared photometers of the antiphase-modulated single-beam type incorporating a detector comprised of two absorption chambers arranged one behind the other.

More specifically, the invention relates to a method of initially adjusting the photometer to render its measurements independent of variations in the composition of the carrier gas accompanying the gas whose concentration is actually to be determined.

Two basically different types of infrared photometers are known, the double-beam type and the single-beam type. These are respectively shown, in schematic form, in FIGS. 1a and 1b.

The double-beam analyzer of FIG. 1a includes two light sources LS, a reference cuvette RC, a measurement cuvette MC, and a detector arrangement comprised of two absorption chambers AC. The measurement cuvette MC contains a mixture of a gas whose concentration is to be measured accompanied by a carrier gas. Reference cuvette RC contains a reference gas. The two beams from the two sources LS are identically modulated (in-phase modulation) by a light chopper LC. The two beams pass through the respective cuvettes MC, RC, and energy in certain spectral portions of the light beam is selectively absorbed. The beams, after emerging from the cuvettes, enter the respective absorption chambers of the detector arrangement. The difference between the pressure pulses induced in the two gas-filled absorption chambers constitutes an indication of the difference between the gases in the two cuvettes, and is measured.

In contrast, the single-beam analyzer of FIG. 1b is provided with only a single light source LS, and a light chopper LC and detector arrangement designed differently than those of FIG. 1a. The light chopper LC modulates the light beams passing through the cuvettes MC and RC identically, but alternately (antiphase modulation). The detector arrangement is again comprised of two absorption chambers, but here arranged one behind the other. As with the double-beam analyzer of FIG. 1a, the difference between the pressure pulses induced in the two absorption chambers of the detector arrangement constitutes an indication of the difference between the gases in the measurement and reference cuvettes, and is measured.

A double-beam analyzer of the type shown in FIG. 1a is disclosed in detail, for example, in German Pat. No. 730,478, filed Mar. 8, 1938. A single-beam analyzer of the type shown in FIG. 1b is disclosed in detail, for example, in U.S. Pat. No. 3,162,761.

With the single-beam apparatus of FIG. 1b, the two absorption chambers are filled with gas, usually a mixture of the gas whose concentration is to be measured along with inert carrier gas. When the light beam passes through the measuring cuvette, there occurs therein a selective absorption of radiation at certain wavelengths corresponding to the infrared-active molecular resonances of the gas whose concentration is to be measured.

The beam emerging from the cuvette then passes through the two absorption chambers of the detector arrangement. In the front chamber, which is shorter than the back chamber, radiation energy is preferentially absorbed at frequencies corresponding to the middle portions of the absorption lines of the gas filling the absorption chamber; in the back absorption chamber, energy is mainly absorbed at frequencies corresponding to the flank portions of the absorption lines of the gas filling the absorption chamber. The absorbed electromagnetic energy is transformed within the absorption chambers into translational energy (heat), producing in the absorption chambers pressures indicative of the absorption energies. The difference between the absorption energies of the two absorption chambers is indicative of the concentration of the gas component of interest in the measurement cuvette.

If the null point of the apparatus is properly established, the output signal from the detector arrangement will be zero when the concentration of the gas component of interest in the measurement cuvette is zero. The null point compensation required to establish a proper null point conventionally involves proper choice of the dimensions of the measuring chamber and proper choice of the concentrations of gases therein.

With a single-beam antiphase-modulated apparatus as shown in FIG. 1b, if the null point has been properly established, the output signal of the detector arrangement will be constant if both the reference cuvette and the measurement cuvette are filled with the reference gas. The radiation passing through the two cuvettes alternately and then entering the common detector arrangement will be the same, so that in superimposition, a constant intensity is sensed by the detector arrangement.

Besides proper establishment of the null point of the gas concentration analyzer, another important operating characteristic is the selectivity of the analyzer. The selectivity of the detector is dependent upon the absorption spectrum of the gas filling the absorption chambers of the detector, and it may be increased by arranging a radiation filter in front of the detector. In recent years, use has been made of interference filters made up of multi-dielectric optically transparent layers of material the transmission of which is limited to predetermined wavelengths. However, the gas to be analyzed often includes, besides the component whose concentration is to be measured, other components whose absorption bands overlap those of the component whose concentration is to be measured. When this is the case, a cross-sensitivity effect may result. To counteract this, filter cuvettes may be interposed in the radiation path.

A further factor of importance to the accuracy of gas concentration measurements performed using such photometers is the so-called collision damping effect. This effect is attributable to the presence of gas components in the measurement cuvette which are not themselves infrared-active, and these components can affect the sharpness of the absorption lines associated with the gas component whose concentration is to be measured.

The collision broadening effect is very briefly explained as follows: The radiation incident in the measurement cuvette is absorbed in specific absorption bands of the gas component whose concentration is to be measured. Collision processes between the molecules which have absorbed radiant energy and other molecules result in a transformation of the absorbed energy into thermal energy within a very short time. The shape of the absorption curve of the gas component whose concentration is to be measured is ordinarily characterized by very fine-structured individual absorption lines, but these are appreciably influenced by such collisions with other molecules, even infrared-inactive molecules in the inert carrier gas in the measurement cuvette. During such a molecular colision, the natural absorption frequencies are temporarily changed by the mutual influence of electromagnetic fields, and the fine-structured absorption lines become temporarily broadened. This has a corresponding effect upon the accuracy and reliability of any measurements which may be performed.

There are additional effects tending to broaden the fine-structured absorption lines, including radiation broadening and Doppler broadening. However, I have found that collision broadening is usually the predominant line-broadening factor in the i.r. range.

As a result of the collision broadening effect, the measurement signal produced by the detector arrangement is not only dependent upon the partial pressure of the gas component whose concentration is to be measured; it is also dependent upon the composition of the carrier gas in the measurement cuvette, even if the carrier gas is entirely inert and exhibits no infrared activity of its own.

The collision broadening effect, because it is attributable to collisions with carrier gas molecules, becomes a very troublesome factor when the gas in the measuring cuvette includes carrier gas components of widely and quickly fluctuating composition. This is the case, for example, when analyzing blast furnace gas, or when analyzing human breath during anesthesia.

In such situations, it may happen that the concentration of the gas component of interest does not change during a certain period of time, but that fluctuations in the composition of the accompanying carrier gas will produce corresponding fluctuations in the output signal of the detector arrangement. For that reason, the reading provided by a photometer in such a situation cannot be considered accurate except within a range corresponding to the possible effect of carrier-gas-composition fluctuations. Therefore, it may be difficult or impossible to reliably detect fluctuations in the concentration of the gas component of interest, if the fluctuations are smaller than would correspond to the possible effect of the fluctuations in the composition of the accompanying carrier gas.

The collision broadening effect also produces difficulties in calibrating the photometer. Conventionally, calibration is performed in the following way. A plurality of calibrating gas samples are obtained. Each calibrating gas sample includes as one component the gas whose concentration is to be measured, and it also includes inert carrier gas of often different compositions from those expected to be encountered during the post-calibration measuring operations. The output signal produced by the two-absorption-chamber detector is noted for each of the different calibrating gas samples, so that during actual measurement there will be available a way of correlating the output signal with known concentrations of the gas whose concentration is to be measured.

This calibrating procedure is complicated by the collision broadening effect, i.e., by the effect of fluctuations in the composition of the infrared-inactive carrier gas in the calibrating gas samples, and in the gas in the measurement cuvette during actual measurements. If two different photometers have been calibrated using calibrating gas samples of non-identical carrier gas composition, the correlation between the detector output signal and the gas concentration reading of one photometer will be different from that of the other photometer. As a result, a series of measurements begun on one photometer cannot be readily continued on the other photometer. Likewise, comparison of the results achieved using one photometer cannot be readily made using the other photometer. This makes it necessary to recalibrate one of the photometers, or else to keep available correlation tables, or the like, to be able to correlate the readings of one instrument with that of the other. Actually, although the invention relates to single-beam analyzers (FIG. 1b), this problem is present with double-beam analyzers (FIG. 1a), as well.

FIG. 2 depicts the effect of fluctuations in carrier gas composition upon the actual gas-concentration measurement for a double-beam analyzer (curve a) and for a single-beam analyzer (curve b). The gas component whose concentration is to be measured (in ppm) is $CO_2$. The carrier gas with which the $CO_2$ in the measurement cuvette is mixed during actual testing is itself a mixture of $O_2$ and $N_2$. However, the relative proportions of $O_2$ and $N_2$ in the carrier gas are assumed to fluctuate greatly during testing. In FIG. 2, $CO_2$ concentration departure from the valve obtained for zero $O_2$ concentration is plotted along the vertical axis, and the proportion of $O_2$ in the $O_2/N_2$ carrier-gas mixture is plotted along the horizontal axis. In this case the actual concentration of $CO_2$ in the $CO_2/O_2/N_2$ mixture was 320 ppm.

It will be noted that the detector output signal correctly indicates departure ppm $CO_2$ only when the carrier gas consists entirely of $N_2$ (the $O_2$ fraction is zero); this is true both for the double-beam analyzer (curve a) and the single-beam analyzer (curve b). As the fraction of $O_2$ in the $O_2/N_2$ carrier-gas mixture increases from 0 to 1.0, the detector output signal changes appreciably, even though the actual $CO_2$ concentration in the measurement cuvette has not left 320 ppm. For the double-beam analyzer (curve a), with its two absorption chambers arranged side by side, the detector output signal decreases as the $O_2$ content in the carrier gas rises. For the single-beam analyzer (curve b), with its two absorption chambers arranged one behind the other, the detector output signal increases as the $O_2$ content in the carrier gas rises. Clearly, fluctuations in the composition of the carrier gas have a very appreciable effect upon the ultimate measurement, in such a situation.

SUMMARY OF THE INVENTION

It is a general object of the invention to provide an infrared analyzer whose readings are more accurate than was the case in the prior art.

According to the broadest aspect of the inventive concept, this is achieved by so designing and/or adjusting the photometer as to make its output signal more or less independent of the composition or concentration of the infrared-inactive carrier gas in the gas sample being tested.

Preferably, the photometer is so adjusted as to render its output signal independent of variations in the relative proportions of the individual components of the multicomponent carrier gas, to below the resolution limit for the entire range from 0–100% of each carries-gas component. For example, if the carrier gas is a two-component gas, it is preferred to achieve carrier-gas-composition independence to below the resolution limit for the entire range of carrier-gas composition, from 0% of the first component and 100% of the second component, up to 100% of the first component and 0% of the second component.

According to the broadest concept of the invention, curve $b$ in FIG. 2 is to be tilted into the horizontal position indicated by the broken line.

According to another concept of the invention, carrier-gas-composition independence is achieved without modifying the design of the single-beam photometer, so that carrier-gas-composition independence may be achieved with photometers already in existence.

This can be achieved, according to the invention, by varying the optical path lengths in the absorption chambers of the detector, either by altering the absorption chamber geometry — e.g., by altering the lengths of the absorption chambers — or else by altering the concentration and/or composition of the gas filling the absorption chambers. In general, the optical path lengths of the absorption chambers are equal to the product of the geometrical path length and the concentration (or partial pressure) of gases in the absorption chambers. Because of the inconvenience of altering the heights of the absorption chambers, it is preferred to achieve carrier-gas-composition independence according to the invention by varying the partial pressures in the absorption chambers.

It is to be emphasized that the concept of achieving independence of carrier-gas composition is itself new and forms the broadest aspect of the invention. In the prior art, comparable photometers have been designed to optimize zero-point constancy, selectivity and reduction of cross-sensitivity. This has diverted the prior art from the inventive concept of establishing carrier-gas-composition independence, because such independence cannot be achieved when zero-point constancy and selectivity are to be maximized. The present invention contemplates achieving carrier-gas-composition independence, even if this is somewhat at the expense of the operating parameters with which the prior art has been concerned.

I have found that the loss in zero-point constancy and/or selectivity resulting from my maximization of carrier-gas-composition independence, if any, is actually quite acceptable. In particular, this is true of single-beam photometers, to which the present invention relates. This is because they are anyway characterized by zero-point constancy and selectivity superior to those of double-beam photometers. Actually, I have found that, when I maximize carrier-gas-composition independence, the reduced zero-point constancy and selectivity of a single-beam photometer will usually still be superior to that of a comparable double-beam photometer.

Thus, to some extent, it is the superiority of single-beam photometers (wherein the absorption chambers are arranged one behind the other) to double-beam photometers (wherein the absorption chambers are arranged side-by-side) that makes photometers modified in accordance with the invention acceptable for the art. In general, single-beam photometers are superior to double-beam photometers with respect to both zero stability and cross-sensitivity.

The reason why single-beam photometers have lower (and therefore superior) cross-sensitivity is the following. Interfering carrier-gas components having a band overlap with the gas whose concentration is to be measured affect the energy absorption in both the front and back absorption chambers, in a manner dependent upon the wavelength position of the overlap for the individual absorption lines. As a result, the cross-sensitivity is in part positive and in part negative, and is inherently compensated for to a great extent, on the average.

The superior zero-point constancy of single-beam photometers with in-series absorption chambers results from the establishing of double differences during the null point compensation. Null point compensation is first effected with respect to the measurement and reference cuvettes. Then there is an additional null point compensation achieved by adjusting the specific energy absorptions in the two absorption chambers of the detector.

As indicated above, single-beam photometers are conventionally designed and adjusted with respect to absorption chamber length, absorption chamber gas concentration and, partial and absolute pressures to maximize selectivity and zero-point constancy.

As also stated above, the present invention, by shifting the emphasis for the first time to carrier-gas-composition independence, at the expense of zero-point constancy and cross-sensitivity, nevertheless achieves a single-beam photometer at least as good in these respects as a comparable double-beam photometer.

DESCRIPTION OF THE PREFERRED EMBODIMENTS

EXAMPLE

The gas component whose concentration is to be measured is $CO_2$ mixed with a carrier gas consisting of $N_2$ and $N_2O$. The concentration of $CO_2$ in the test gas was expected to vary within the range 0 – 10%. The relative proportions of $N_2$ and $N_2O$ in the carrier gas were known to fluctuate considerably. This is the gas in the measurement cuvette.

The in-series absorption chambers are each filled with the gas whose concentration is to be measured ($CO_2$) in mixture with Ar.

First proceeding in accordance with the prior art, the concentration of $CO_2$ was selected to maximize zero-point constancy and selectivity, as discussed above. For the example in question, the $CO_2$ concentration in the absorption chambers would conventionally be set to about 2 – 3%. In the present example, it was set to 2.5%.

Measurements were then made upon two test gas specimens, one having the composition 10% $CO_2$, 20% $N_2O$, 70% $N_2$, and the other having the composition 10% $CO_2$, 70% $N_2O$, 20% $N_2$. It was found that the $CO_2$ concentration measurements in the two cases were markedly different, even though the actual $CO_2$ concentration was 10% in each case.

To establish carrier-gas-composition independence, the following was done:

The concentration of $CO_2$ in the absorption chambers was raised from the conventionally selected value of 2.5% up to 15%. CO₂ concentration measurements were then performed using a series of test gases having the following compositions:

10% $CO_2$, 20% $N_2$, 70% $N_2O$
10% $CO_2$, 45% $N_2$, 45% $N_2O$
10% $CO_2$, 70% $N_2$, 20% $N_2O$.

Figure 1A:
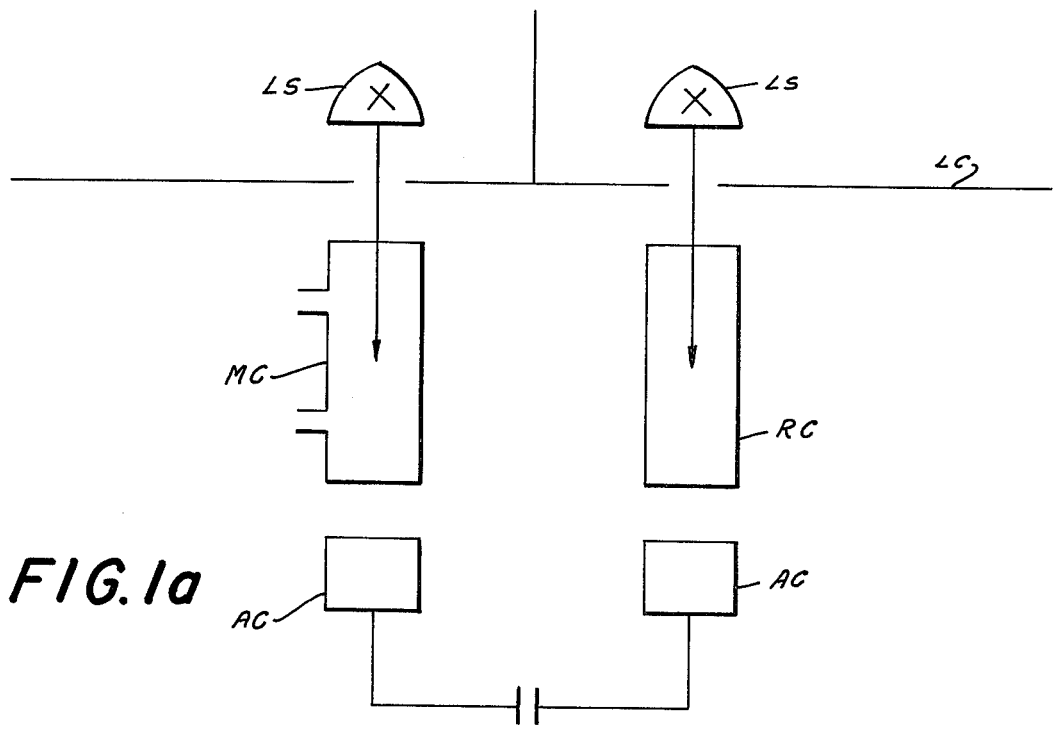
FIGS. 1$a$ and 1$b$ depict a double-beam photometer, and a single-beam photometer, respectively.
Figure 1B:
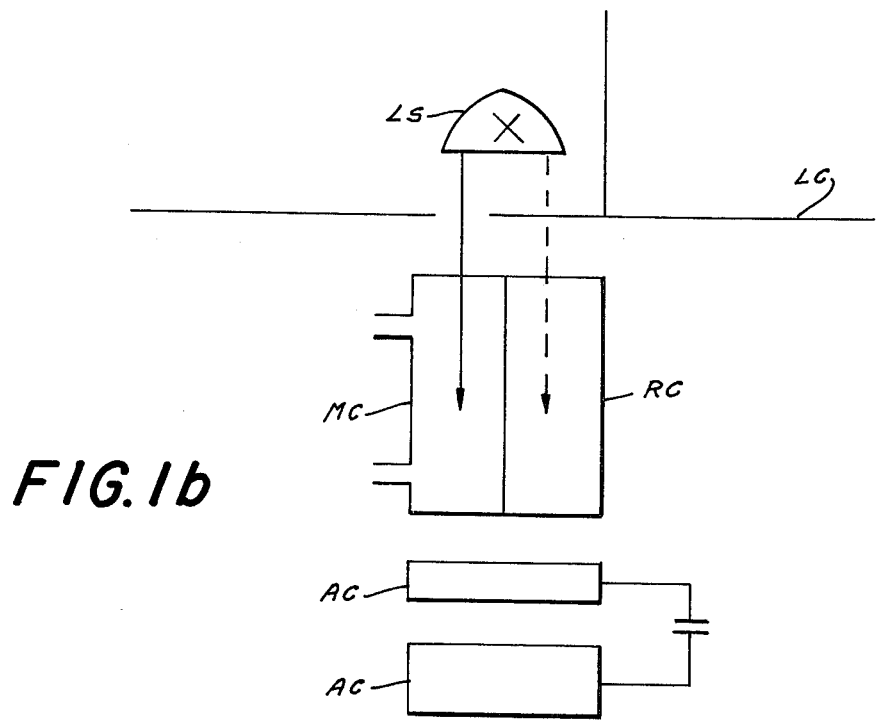
Figure 2:
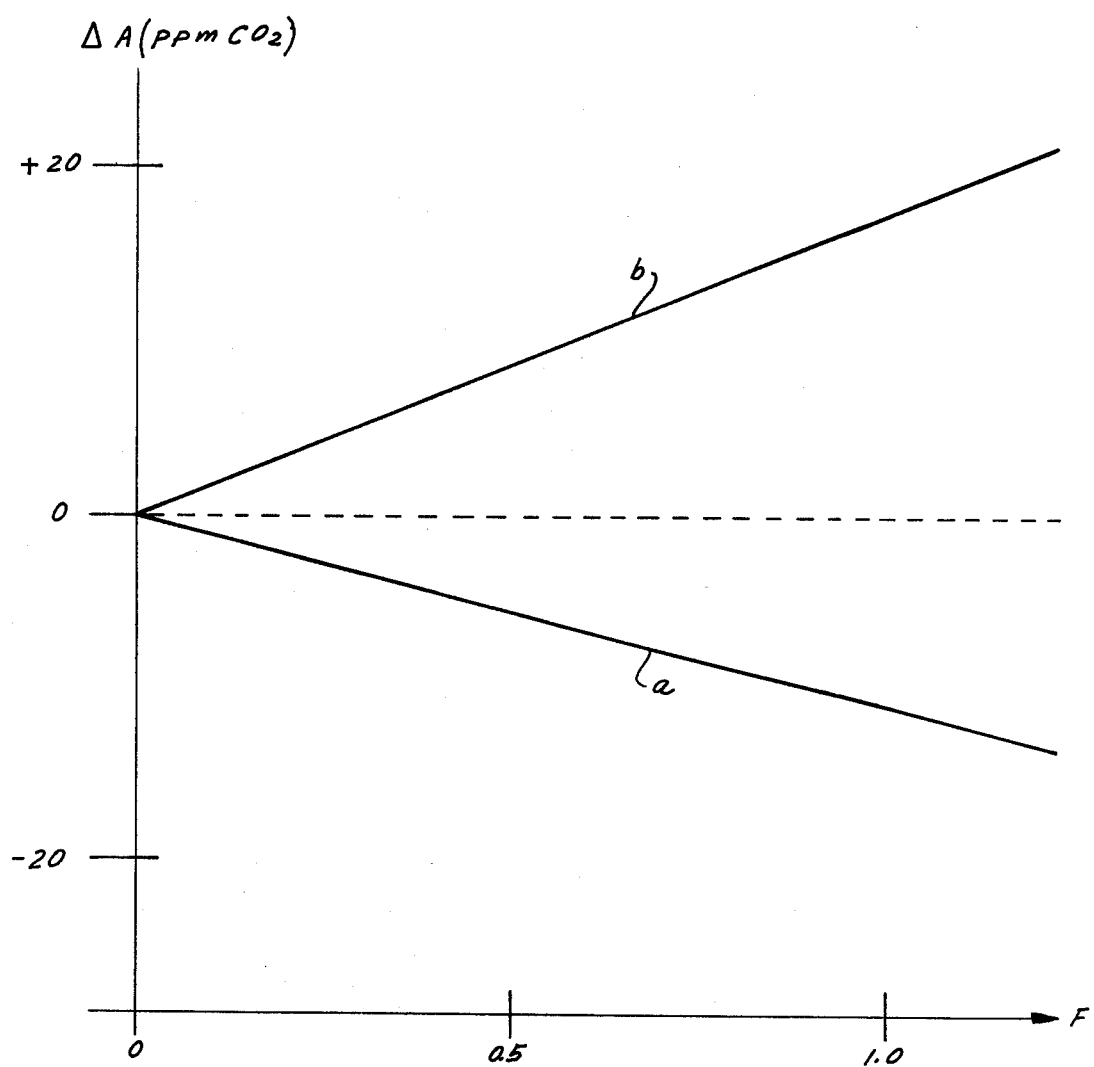
FIG. 2 depicts the dependence of the photometer output signal upon carrier-gas-composition variations.

The results of the $CO_2$ concentration measurements were plotted in a curve like curve $b$ of FIG. 2. It was found that the curve deviated markedly from the horizontal.

This procedure was repeated, using the same series of test gas compositions, but with different concentrations of $CO_2$ in the $CO_2$/Ar mixture in the absorption chambers. Interpolation and extrapolation were used to determine when the $CO_2$ concentration in the absorption chambers needed to be raised or needed to be lowered, to make the curve corresponding to curve $b$ of FIG. 2 more nearly horizontal.

Eventually, 7.5% was selected for the concentration of $CO_2$ in the $CO_2$/Ar mixture in the absorption chambers. With this concentration, it was found that the carrier-gas-composition dependence was reduced to below the resolution limit over the total range of 0 – 100% $N_2O$ in $N_2$.

Generally, I have found that after at most three trials acceptable carrier-gas-composition independence will be reached.

It is to be noted that, when achieving such independence by varying the $CO_2$ concentration in the absorption chambers, the concentration in both absorption chambers was identically varied. Also, the pressures in the two absorption chambers were equal, because these chambers are connected by a capillary tube exhibiting a large time constant to prevent static pressure differences between the two absorption chambers. In general, absolute pressures and temperatures in the two absorption chambers are not critical, although the absolute pressure and temperature in the one chamber should be equal to those in the other.

In the foregoing example, carrier-gas-composition independence was achieved exclusively by repeatedly changing the concentration of $CO_2$ in Ar in the absorption chambers. Alternatively, such independence could be achieved by changing the lengths of the two absorption chambers. However, that would ordinarily involve changes in construction, and therefore is not preferred. Because the optical path length is the product of gas concentration and geometrical path length, it is sufficient to adjust only the gas concentration.

It has been found that carrier-gas-composition independence is most advantageously achieved by an empirical procedure such as described in the Example above. This procedure is not purely a trial-and-error procedure, but rather is more nearly a true iterative procedure; each time the gas concentration in the absorption chambers is selected, the result of that selection, by interpolation or extrapolation, points the way to the next gas concentration selection, so that relatively few experimental selections need be performed.

This empirical technique is very advantageous. Corresponding compensation techniques based upon calculation would be extremely complicated or practically impossible to perform, because in general the exact details of the structure of the absorption spectra will not be known. Moreover, even if known, the calculations themselves would be excessively complicated. Nevertheless, some theoretical comments can be made with respect to what occurs as the carrier-gas-composition independence is being established.

If the sample gas in the measurement cuvette includes a component which broadens an absorption line of the gas component whose concentration is to be measured, there will also result an increase in the amplitude of the absorption line. The molecules of the gas whose concentration is to be measured, when excited in the measurement cuvette, have greater possibilities of transferring their energy by collision to the carrier gas molecules. As a result, both the amplitude and width of the absorption line are increased. With the two absorption chambers of the single-beam detector being arranged in series, the increased absorption line amplitude results in a decrease of the component of the measurement signal associated with the front absorption chamber; the increased line width results in a decrease of the measurement signal component associated with the back absorption chamber.

It is these effects which are brought into balance, to achieve carrier-gas-composition independence, when the gas concentration in the absorption chambers is varied in accordance with the empirical technique set forth in the Example above. In general, the technician setting up the photometer for carrier-gas-composition independence will not separately concern himself with the absorption line widths and amplitudes for the measurement cuvette and absorption chamber gases. Neverthless, when he performs the setting-up procedure described above, what he is doing is bringing about a certain relationship, not readily brought about by calculation, as between the line widths of the measurement cuvette and absorption chamber gases. It is this absorption line width relationship which, more than anything else, is the condition which actually results in carrier-gas-composition independence.

Again, it is to be noted that the method of the invention can be performed quite inexpensively when the inventive carrier-gas-composition independence is brought about by changing the optical path lengths of the detector absorption chambers only, and particularly when the optical path lengths are changed exclusively by changing the concentration of the gas whose concentration is to be measured.

It will be understood that each of the elements described above, or two or more together, may also find a useful application in other types of methods and constructions differing from the types described above.

While the invention has been illustrated and described as embodied in a setting up a photometer for carrier-gas-composition independence, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method of setting up a non-dispersive infrared photometer of the type comprised of a light source, a reference cuvette containing a reference gas, a measurement cuvette containing an infrared-active gas component whose concentration is to be measured accompanied by a carrier gas, the carrier gas comprising at least one component which is infrared-inactive, a light modulator for effecting antiphase modulation of the light passing through the two cuvettes, and a detector arrangement comprised of two gas-filled absorption chambers arranged one behind the other and a transducer for converting pressure changes induced in the absorption chambers into a measurement signal, the method comprising the step of adjusting the photometer to render the measurement signal substantially independent of the composition of the carrier gas in the measurement cuvette.

2. A method of setting up a non-dispersive infrared photometer of the type comprised of a light source, a reference cuvette containing a reference gas, a measurement cuvette containing a gas component whose concentration is to be measured accompanied by a carrier gas, a light modulator for effecting antiphase modulation of the light passing through the two cuvettes, and a detector arrangement comprised of two gas-filled absorption chambers arranged one behind the other and a transducer for converting pressure changes induced in the absorption chambers into a measurement signal, the method comprising the step of adjusting the photometer to render the measurement signal substantially independent of the composition of the carrier gas in the measurement cuvette, the adjusting step comprising adjusting only the absorption chambers of the detector.

3. A method of setting up a non-dispersive infrared photometer of the type comprised of a light source, a reference cuvette containing a gas component whose concentration is to be measured accompanied by a carrier gas, a light modulator for effecting antiphase modulation of the light passing through the two cuvettes, and a detector arrangement comprised of two gas-filled absorption chambers arranged one behind the other and a transducer for converting pressure changes induced in the absorption chambers into a measurement signal, the method comprising the step of adjusting the photometer to render the measurement signal substantially independent of the composition of the carrier gas in the measurement cuvette, the adjusting step comprising adjusting the optical path-lengths of the absorption chambers.

4. The method defined in claim 3, the optical path-lengths of the absorption chambers being adjusted by altering the geometrical path-lengths of the absorption chambers.

5. The method defined in claim 3, the absorption chambers containing gas of the same composition as the gas whose concentration is to be measured but accompanied by an inert gas, the optical path-lengths of the absorption chambers being adjusted by altering the concentration in the absorption chambers of the gas of the same composition as the gas whose concentration is to be measured.

6. The method defined in claim 3, the absorption chambers containing gas of the same composition as the gas whose concentration is to be measured but accompanied by an inert gas, the opticl path-lengths of the absorption chambers being adjusted by altering the partial pressure in the absorption chambers of the gas of the same composition as the gas whose concentration is to be measured.

7. A method of setting up a non-dispersive infrared photometer of the type comprised of a light souce, a reference cuvette containing a reference gas, a measurement cuvette containing a gas component whose concentration is to be measured accompanied by a carrier gas, a light modulator for effecting antiphase modulation of the light passing through the two cuvettes, and a detector arrangement comprised of two gas-filled absorption chambers arranged one behind the other and a transducer for converting pressure changes induced in the absorption chambers into a measurement signal, the method comprising the step of adjusting the photometer to render the measurement signal substantially independent of the composition of the carrier gas in the measurement cuvette, the adjusting step comprising adjusting the photometer to render the measurement signal independent of the carrier-gas composition to below the resolution limit.

8. A method of setting up a non-dispersive infrared photometer of the type comprised of a light source, a reference cuvette containing a reference gas, a measurement cuvette containing a gas component whose concentration is to be measured accompanied by a carrier gas, a light modulator for effecting antiphase modulation of the light passing through the two cuvettes, and a detector arrangement comprised of two gas-filled absorption chambers arranged one behind the other and a transducer for converting pressure changes induced in the absorption chambers into a measurement signal, the method comprising the step of adjusting the photometer to render the measurement signal substantially independent of the composition of the carrier gas in the measurement cuvette, the carrier gas consisting predominantly of a first gas component in a second gas component, the adjusting step comprising adjusting the photometer to render the measurement signal independent of the carrier-gas composition to below the resolution limit for the entire range of 0 – 100% of the first gas component in the second gas component.

9. A method of setting up a non-dispersive infrared photometer of the type comprised of a light source, a reference cuvette containing a reference gas, a measurement cuvette containing a gas component whose concentration is to be measured accompanied by a carrier gas, a light modulator for effecting antiphase modulation of the light passing through the two cuvettes, and a detector arrangement comprised of two gas-filled absorption chambers arranged one behind the other and a transducer for converting pressure changes induced in the absorption chambers into a measurement signal, the method comprising the step of adjusting the photometer to render the measurement signal substantially independent of the composition of the carrier gas in the measurement cuvette, the carrier gas consisting of a plurality of gas components, the absorption chambers each containing a gas identical to the gas whose concentration is to be measured accompanied by an inert gas, the adjusting step comprising obtaining a plurality of test gas samples, each test gas sample having the same concentration of the gas component whose concentration is to be measured, but different relative proportions of the components of the carrier gas, successively introducing each of the test gas samples into the measurement cuvette and performing a photometric measurement of the concentration of the gas component whose concentration is to be measured, determining the dependence of the measurement signal upon the differences in the relative proportions of the components of the carrier gas, based upon that determination changing the concentration in the absorption chambers of the gas identical to the gas whose concentration is to be measured, again performing photometric gas concentration measurements using the test gas samples, again determining the dependence of the detector output signal upon the carrier-gas composition, based upon the last-mentioned determination again changing the concentration of the gas in the absorption chamber, and repeating these steps until the output signal of the detector is made substantially independent of carrier-gas composition changes.

10. A method of setting up a non-dispersive infrared photometer of the type comprised of a light source, a reference cuvette containing a reference gas, a measurement cuvette containing a gas component whose concentration is to be measured accompanied by a carrier gas, a light modulator for effecting antiphase modulation of the light passing through the two cuvettes, and a detector arrangement comprised of two gas-filled absorption chambers arranged one behind the other and a transducer for converting pressure changes induced in the absorption chambers into a measurement signal, the method comprising the step of adjusting the photometer to render the measurement signal substantially independent of the composition of the carrier gas in the measurement cuvette, the carrier gas in the measurement cuvette consisting of a plurality of carrier-gas components, the adjusting step comprising adjusting the photometer to render the measurement signal substantially independent of the relative proportions of the carrier-gas components.

* * * * *